US007758733B2

(12) United States Patent
Hsiung et al.

(10) Patent No.: US 7,758,733 B2
(45) Date of Patent: Jul. 20, 2010

(54) DUAL TYPE POTENTIOMETRIC CREATININE BIOSENSOR

(75) Inventors: Shen-Kan Hsiung, Tao-Yuan (TW);
Jung-Chuan Chou, Tao-Yuan (TW);
Tai-Ping Sun, Tao-Yuan (TW);
Chung-Wei Pan, Tao-Yuan (TW);
Nien-Hsuan Chou, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 1040 days.

(21) Appl. No.: 11/457,589

(22) Filed: Jul. 14, 2006

(65) Prior Publication Data

US 2007/0158213 A1 Jul. 12, 2007

(30) Foreign Application Priority Data

Jan. 2, 2006 (TW) .............................. 95100102 A

(51) Int. Cl.
*G01N 27/327* (2006.01)
*G01N 27/333* (2006.01)
(52) U.S. Cl. .................................. 204/403.05; 204/416
(58) Field of Classification Search ................................ 204/403.01–403.15, 416–419; 205/777.5, 205/778, 792; 257/253
See application file for complete search history.

(56) References Cited

OTHER PUBLICATIONS

Magalhães et al. "Array of potentiometric sensors for the analysis of creatinine in urine samples," Analyst, 2002, 127, 1069-1075.*
Pandey et al. "Novel potentiometric sensing of creatinine," Sensors and Actuators B 99 (2004) 230-235.*
Radomska et al. ("Creatinine biosensor based on ammonium ion selective electrode and its application in flow-injection analysis," Talanta 64 (2004) 603-608).*
Shih et al. ("A Creatinine deiminase modified polyaniline electrode for creatinine analysis," Analytica Chimica Acta 392 (1999) 143-150).*
Nien Hsuan Chou, Jung Chuan Chou, Tai Ping Sun, Shen Kan Hsiung, [Study on a dual pH/NH+4 electrode-based disposable potentiometric biosensor for the creatinine], Conference Name: Proceedings of The Abstracts of The 3rd International Conference on Materials for Advanced Technologies (ICMAT 2005); The 9th International Conference on Advanced Materials (ICAM 2005), Conference Place: International Convention & Exhibition Centre; Singapore, Publish Date: May 28, 2005, Conference Date: Jul. 2005, Nsc Plan Number :NSC.

* cited by examiner

*Primary Examiner*—Alex Noguerola
(74) *Attorney, Agent, or Firm*—WPAT, PC; Justin King

(57) ABSTRACT

In this invention, a separative structure of the ion-selecting electrode is applied to fabricate the dual type potentiometric biosensor for creatinine detection. According to the fabrication process, the creatinine enzyme is immobilized onto a conductive layer of a substrate of pH sensing membrane and ammonium ion-selecting membrane. The conductive layer provides with a sensing region and a non-sensing region. A conductive line is extended from the conductive layer for using as an external electrical contact point. The dual type potentiometric creatinine biosensor was fabricated by using the enzyme immobilization method onto the surface of the selecting membrane of sensing membrane of pH sensing electrode and creatinine sensor.

2 Claims, 6 Drawing Sheets

DUAL TYPE POTENTIOMETRIC CREATININE BIOSENSOR

CROSS REFERENCE TO RELATED APPLICATIONS

N/A

BACKGROUND OF THE INVENTION

1. Field of the Invention

The invention relates in general to a sensing apparatus. More particularly, this invention relates to a dual type potentiometric biosensor for creatinine detection and fabricating methods thereof, which biosensor is based on an ion-selecting electrode.

2. Description of the Prior Art

A model of a biosensor is based on an analytic method of detecting a new organic compound. The analytic method was established by using the specificity theory of an enzyme and its substrate. This specificity theory is proposed by Clark et al. in 1962 (Clark L. C., C. Lyois, "Electrode system for continuous monitoring in cardiovascular surgery", Annals of the New York Academy of Sciences, vol. 102, pp. 29-33, 1962.).

In recent years, as an electronic technology vigorously developed, a biochemistry technology has already further applied to a design of a sensor. In clinical detection of a healing institute, creatinine is one of major indexes for detecting a kidney failure of a human body. On one hand, when the creatinine density is more than 140 micro volumes Mole density ($\mu M$) above in the blood and keeps rising, it entered time of a chronic renal failure. On the other hand, by the detection of creatinine, protein absorption and dissimilation appear. The detection of creatinine simultaneously relates to functions of a kidney and a liver function, and relates to internal-secretion function of an adrenal gland. Therefore, a function of a kidney can be evaluated, if a biosensor is developed to detect creatinine. The enzyme method is more convenient than a spectral analysis method, although the spectral analysis method can be applied to directly detect a concentration of creatinine.

One of Intechno Cunsulting investigation reports (Zhang Chen-Sui, market demand and technology-developing tendency of sensors, Industrial Economics & Knowledge Center, 2002.) shows that the world market of sensors grew from 325 hundred million US dollars in 1998, to 422 hundred million US dollars in 2003. If a biotechnology combines with a semiconductor technology after devices are formed to have small sizes, products may have advantages of small volumes small, small weights, high reliabilities, high precision, low temperature and light effects, good performance, low costs is low as well as mass production. Such products have high usability in medical detection.

Accordingly, in the industry, there is a need to develop a dual type potentiometric creatinine biosensor, which biosensor is applied with a semiconductor technology. The semiconductor-combined biosensor accurately determines the concentration a sample solution, through a simple procedure.

SUMMARY OF THE INVENTION

Therefore, in accordance with the previous summary, objects, features and advantages of the present disclosure will become apparent to one skilled in the art from the subsequent description and the appended claims taken in conjunction with the accompanying drawings.

A dual type potentiometric creatinine biosensor is provided according to the present invention. The biosensor is based on a plurality of ion electrodes. The biosensor comprises a substrate, a first sensing membrane a conductive line, a second sensing membrane, a first creatinine enzyme membrane, a second creatinine enzyme membrane and a readout circuit. The first sensing membrane is for detecting a plurality of conductive and solid state ions, the first sensing membrane being formed on the substrate. The first sensing membrane is for detecting a pH value of a solution. The first sensing membrane has a region serving as a sensing region. The conductive line, formed on the substrate, is packaged with the sensing membrane. The conductive line is for serving as an external electrical contact point. The second sensing membrane, for detecting a plurality of ammonium ions, is formed on the sensing region of the packaged sensing membrane. The second sensing membrane serves as an ion-selecting and sensing region for detecting the ammonium ions. The first creatinine enzyme membrane is formed on the ion-selecting and sensing region, to complete a first creatinine sensor. The second creatinine enzyme membrane is formed on the sensing region of the sensing membrane, to complete a second creatinine sensor. The first creatinine sensor and the second creatinine sensor are for generating signals. The readout circuit, connected to the conductive line, is for reading the signals generated form the first creatinine sensor and the second creatinine sensor.

Both the foregoing general description and the following detailed description are exemplary and explanatory only and are not restrictive of the invention, as claimed.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Figure 1:
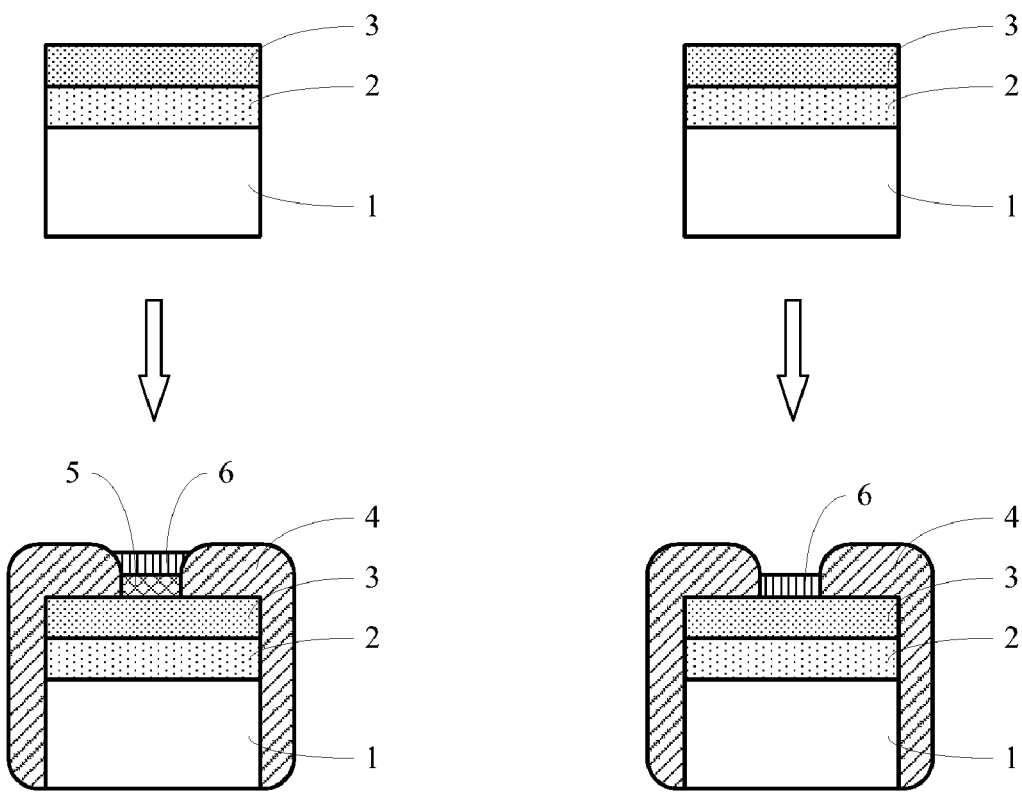
FIG. 1 is a flowchart showing a process of fabricating a creatinine sensor with a pH sensing electrode, and a process of fabricating a creatinine sensor with an ammonium ion-selecting electrode.

The present disclosure can be described by the embodiments given below. It is understood, however, that the embodiments below are not necessarily limitations to the present disclosure, but are used to a typical implementation of the invention.

It is noted that the drawings presents herein have been provided to illustrate certain features and aspects of embodiments of the invention. It will be appreciated from the description provided herein that a variety of alternative embodiments and implementations may be realized, consistent with the scope and spirit of the present invention.

It is also noted that the drawings presents herein are not consistent with the same scale. Some scales of some components are not proportional to the scales of other components in order to provide comprehensive descriptions and emphasizes to this present invention.

First Embodiment

I. Fabrication of a pH Sensing Electrode (1) An indium tin oxide 2/a glass substrate 1: The thickness of the indium tin oxide 2 is about 230 angstroms (Å).

(2) The size of a sensing window is about 3×3 mm$^2$.

(3) Conditions for manufacturing a tin-dioxide sensing membrane 3:

A tin dioxide membrane is grown by a sputtering method with a target made of tin dioxide. A gas mixture of the argon and the oxygen (4:1) is introduced.

When the tin dioxide membrane is grown, the temperature of the substrate is maintained at about 150° C. Additionally, the deposition pressure is maintained at 20 mtorrs, the radio frequency power is about 50 watts, the membrane thickness is about 2,000 angstroms.

II. Fabrication of an Ammonium Ion-Selecting Electrode (1) Carboxylated Poly(vinyl chloride) (PVC-COOH) or Poly(vinyl chloride) (PVC), Bis(2-ethylhexyl) sebacate (DOS), and ammonium ion selector (Nonactin), with proportions of about 33%, 66% and 1%, are mixed and stirred. A solvent, 0.375 ml tetrahydrofuran (THF), is added and is then mixed by a supersonic oscillator.

(2) 1.0 microliters (μL) to 2.0 microliters (μL) ammonium-ions-mixed solution of the step (1) is taken out. The solution is dropped onto the sensing region of the pH sensing electrode, which electrode is made of the tin-dioxide sensing membrane 3/indium tin oxide 2/glass substrate 1.

(3) The device is introduced into a dark chamber under 25° C. for about 12 to 24 hours, thereby completing a fixing process of the ammonium ion electrode, to form an ammonium ion-selecting membrane 5.

III. Fabrication of a Dual Type Potentiometric Creatinine Biosensor:

(1) PVA-SbQ is diluted (125 milligrams (mg)/100 microliter (μL) phosphate solution, with a pH value about 7.5 and a concentration of about 5 μM). The phosphate solution is mixed with a 10 milligrams (mg)/100 microliter (μL) enzyme solution, with a proportion of 1:1. The enzyme solution has a pH value of about 7.5 and a concentration of about 5 μM.

(2) 1.0 microliters (μL) of the mixing solution of step (1) is dropped onto the surface of the sensing region of the ammonium ion-selecting electrode. The mixing solution is vertically illuminated by a 365 nanometers (nm) ultraviolet ray, with 4 watts, to perform a photopolymerization reaction for about 20 minutes. In this photopolymerization reaction, a polyvinyl alcohol may be formed.

(3) After step (2), the device is introduced into a dark chamber having a temperature of about 4° C. for about 12 hours, so that the enzyme-fixing process is completed. In this process, a creatinine enzyme membrane 6 is formed.

EXAMPLE 1 FABRICATION OF A CREATININE SENSOR (1) A tin dioxide membrane is grown to have a thickness of about 2000 angstroms by a sputtering method, to complete the fabrication of a pH sensing electrode.

(2) Carboxylated Poly(vinyl chloride) (PVC-COOH) or Poly(vinyl chloride) (PVC), Bis(2-ethylhexyl) sebacate (DOS), and ammonium ion selector (Nonactin), with proportions of about 33%, 66% and 1%, are mixed and stirred. Carboxylated Poly(vinyl chloride) (PVC-COOH) or Poly(vinyl chloride) (PVC), Bis(2-ethylhexyl) sebacate (DOS), and ammonium ion selector (Nonactin), with proportions of about 33%, 66% and 1%, are mixed and stirred.

(3) A solvent, 0.375 ml tetrahydrofuran (THF), is added and is then mixed by a supersonic oscillator. A 1.0 microliters (μL) to 2.0 microliters (μL) ammonium-ions-mixed solution of the step (2) is taken out. The solution is dropped onto the sensing region of the pH sensing electrode, which electrode is made of the tin-dioxide sensing membrane/indium tin oxide/glass substrate. The device is introduced into dark chamber under a room temperature for about 12 to 24 hours.

(4) By using a technology of fixed ion selecting electrode membrane, the creatinine enzyme is fixed on the pH ion electrode membrane and ammonium ion selecting electrode membrane. PVA-SbQ is diluted to be a 5 mM phosphate solution. The phosphate solution has a concentration of 125 milligrams (mg)/100 microliter (μL), and has a pH value of about 7.0. The phosphate solution is mixed with an enzyme solution, by a proportion of 1:1. The enzyme solution, has a concentration of 10 milligrams (mg)/100 microliter (μL) (5 mM), and has a pH value of about 7.0

(5) 1.0 microliters of the mixing solution of step (4) is dropped onto the sensing region of the ammonium ion selecting electrode. The device is illuminated by a 365 nanometers (nm) ultraviolet ray with 4 watts, to perform a photopolymerization reaction for about 20 minutes. After the reaction is performed, the device is introduced into a dark chamber under 4° C. for about 12 hours, so that an enzyme-fixing process is completed.

EXAMPLE 2 DETECTION BY CREATININE SENSOR

When solutions with the different creatinine concentrations are detected by a creatinine sensor, different detecting results come out. The detecting results are obtained by measuring the output signals of different pH values by a signal-picking device. The device is, for example, a commercialized instrument amplifier circuit LT1167 is used as a readout circuit.

Figure 6:
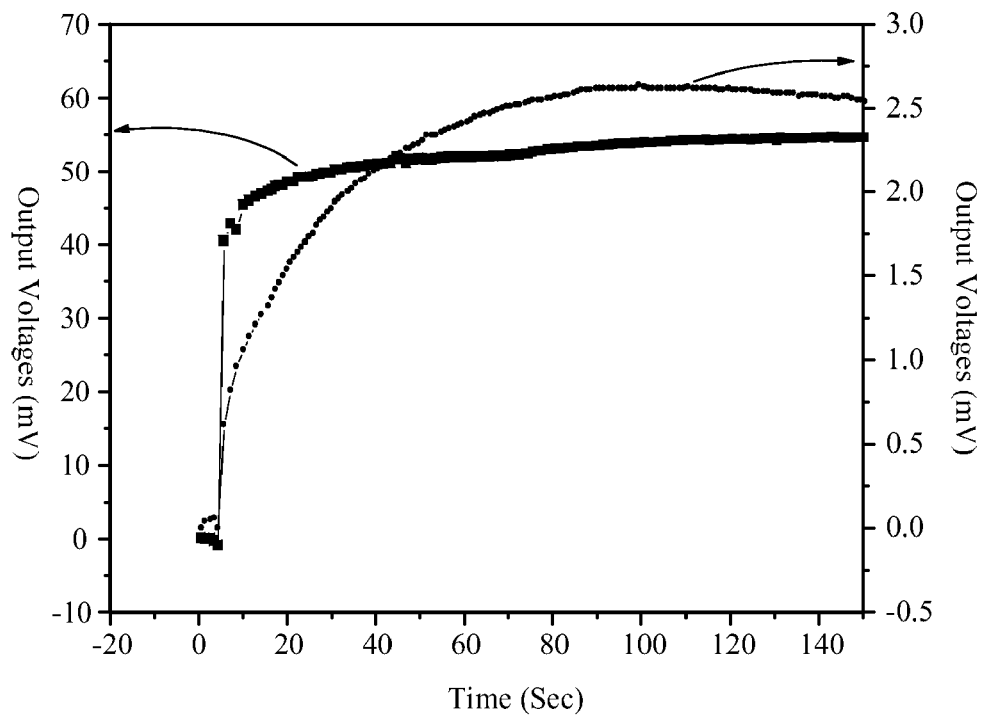
FIG. 6 is a plot showing curves of output voltages of a dual type potentiometric biosensor for creatinine detection with respect to duration.

FIG. 6 is a plot showing curves of output voltages of a biosensor for creatinine detection with respect to duration. The curves are obtained respectively by using a pH sensing electrode and an ammonium electrode. The detecting range of the biosensor is from about 15 to about 185 μM. Accordingly, the creatinine sensor fabricated according to the present invention has good characteristics.

Second Embodiment

Figure 9:
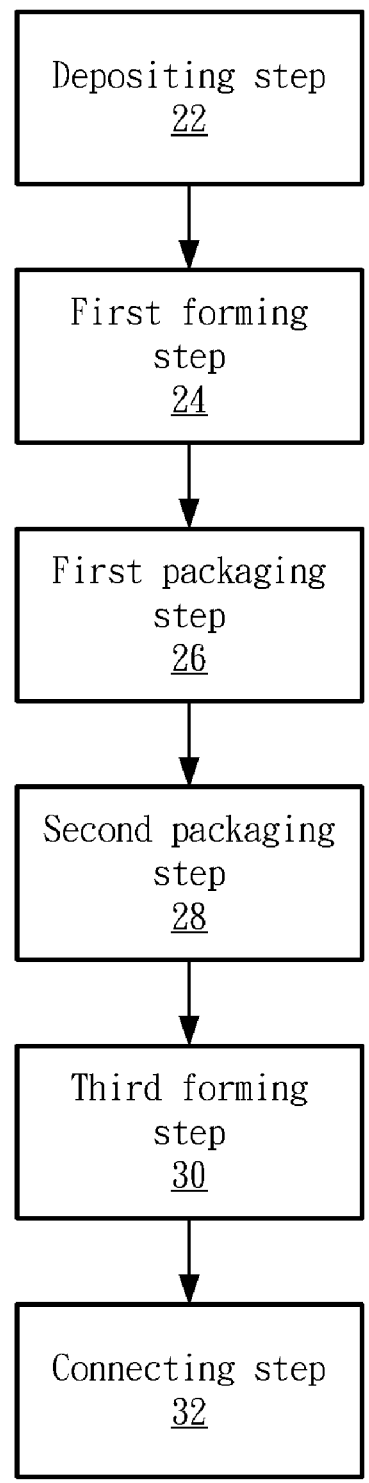
FIG. 9 is a flowchart showing a process of fabricating a biosensor according to a preferred embodiment of the present invention.

FIG. 9 is a flowchart showing a process of fabricating a biosensor according to a preferred embodiment of the present invention. Referring to FIG. 9, a depositing step 22 is performed to deposit a sensing membrane on a substrate, wherein the sensing membrane is for detecting a plurality of conductive and solid state ions. A first forming step 24 is performed to form a conductive line on the substrate. A first packaging step 26 is performed to package the conductive line with the sensing membrane, wherein the conductive line serves as an external electrical contact point. A second packaging step 28 is performed to partially package the substrate, the sensing membrane and the conductive line with a package material, thereby leaving a first sensing region and a second sensing region. A second forming step 30 is performed to form a sensing membrane for detecting a plurality of ammonium ions on the second sensing region, wherein the formed sensing membrane serves as an ion-selecting and sensing region for detecting the ammonium ions. A third forming step 30 is performed to form a first creatinine enzyme membrane on the sensing membrane and the second sensing region, by a photo-polymerisation reaction. A connecting step 32 is performed to connect a readout circuit to the conductive line.

Third Embodiment

Figure 10:
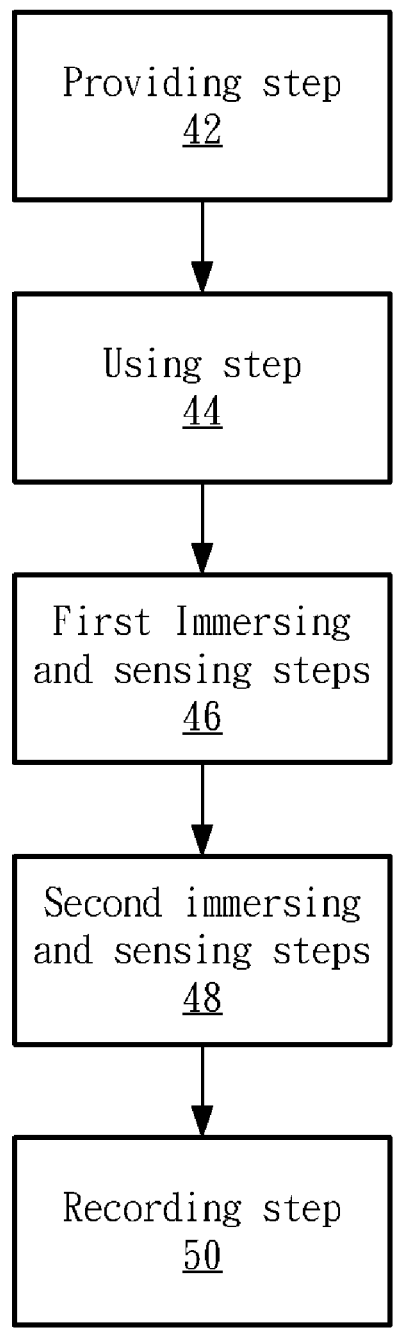
FIG. 10 is a flowchart showing a process of detecting a creatinine solution according to a preferred embodiment of the present invention.

FIG. 10 is a flowchart showing a process of detecting a creatinine solution according to a preferred embodiment of the present invention. Referring to FIG. 10, a providing step 42 is performed to provide a biosensor comprising the following devices. A substrate; a sensing membrane for detecting a plurality of conductive and solid state ions, the sensing membrane being deposited on the substrate, the sensing membrane having a region serving as a sensing region; a conductive line, formed on the substrate, packaged with the sensing membrane; a sensing membrane for detecting a plurality of ammonium ions, formed on the sensing region of the packaged sensing membrane; a first creatinine enzyme membrane, formed on the ion-selecting and sensing region, to complete a first creatinine sensor; and a second creatinine enzyme membrane, formed on the sensing region of the sensing membrane, to complete a second creatinine sensor, wherein the first creatinine sensor and the second creatinine sensor are for generating signals.

A using step 44 is performed to use an amplifier as a readout circuit of the biosensor. A first immersing and sensing steps 46 is performed. The immersing step is performed to partially immerse and then stabilize the biosensor in a buffer solution. The first sensing step is performed to sense a first output voltage of the buffer solution by the sensor, wherein the output voltage serves as a standard voltage. A second immersing and sensing steps 48 is performed. The second immersing step is performed to partially immerse the biosensor in the creatinine solution. The second sensing step is performed to sense a second output voltage of the buffer solution by the biosensor. A recording step 50 is performed to record the second output voltage by the first creatinine sensor or the second creatinine sensor.

As shown in FIG. 1, a flowchart shows a process of fabricating a creatinine sensor with a pH sensing electrode, and a process of fabricating a creatinine sensor with an ammonium ion-selecting electrode. In the present invention, the fabricating processes may be easily performed. The electrodes may be easily packaged. The cost may be reduced. The biosensor can be a disposable type.

The numbers of FIG. 1: glass substrate 1; indium tin oxide 2; tin-dioxide sensing membrane 3; epoxy resin 4; ammonium ion-selecting membrane 5; creatinine enzyme membrane 6. The epoxy resin 6 is a kind of thermal setting resin. A thermal setting resin may be a material for making the glass substrate 1, the ammonium ion-selecting membrane 5 and a conductive line 8 (FIG. 2).

Figure 2:
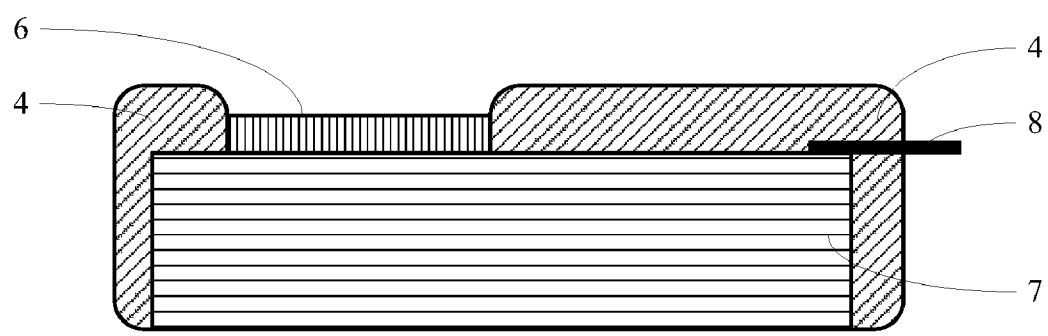
FIG. 2 shows a schematic cross-section of a potentiometric creatinine sensor according to a preferred embodiment of the present invention.

FIG. 2 shows a schematic cross-section of a potentiometric creatinine sensor according to a preferred embodiment of the present invention. The numbers in FIG. 1: a pH sensing/ammonium ion-selecting electrode 7; a conductive line 8.

Figure 3:
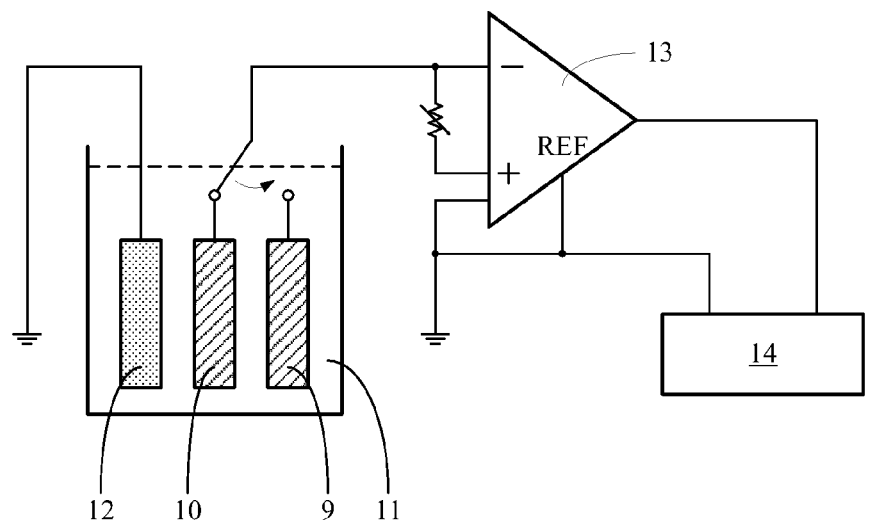
FIG. 3 is a schematic diagram showing a measurement configuration of a dual type potentiometric biosensor for creatinine detection according to a preferred embodiment of the present invention.

FIG. 3 is a schematic diagram showing a dual type potentiometric biosensor for creatinine detection. A readout circuit of the biosensor is an instrument amplifier. The instrument amplifier has a negative input end connected with the biosensor. A silver/silver chloride electrode is provided to generate a reference stabilizing potential. Accompanying with the silver/silver chloride electrode, the reaction voltage for detecting can be switched. The readout circuit is alternatively a potentiometric amplifier or a differential amplifier. The numbers of FIG. 3: a potentiometric biosensor for creatinine detection 9 fabricated by a pH sensing electrode/pH sensing electrode; a potentiometric biosensor for creatinine detection 10 an ammonium ion-selecting electrode/ammonium ion-selecting electrode; a detectable creatinine solution 11; a silver/silver chloride electrode 12; an instrument amplifier 13; a digital light meter 14 with multi-functions.

Figure 4:
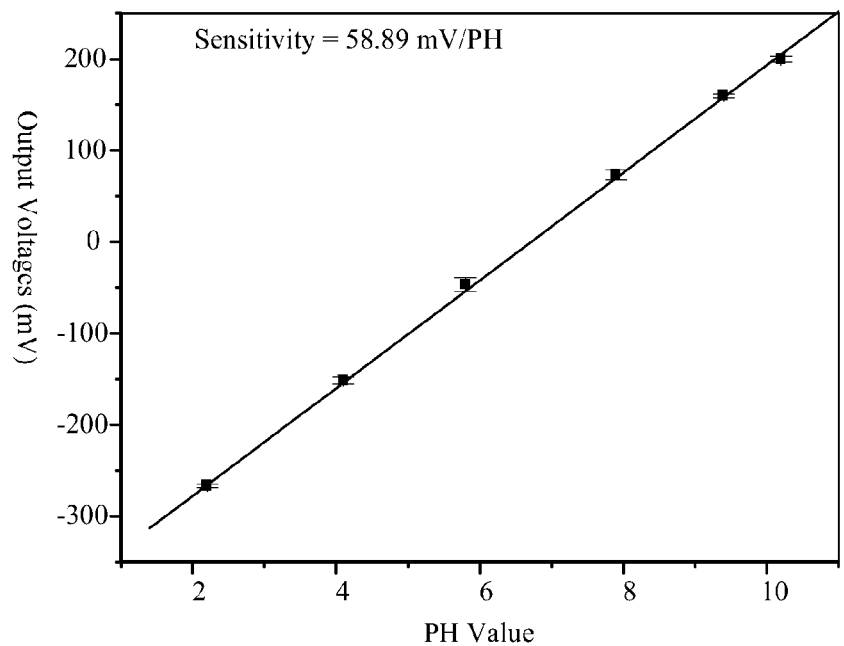
FIG. 4 is a plot showing a linear-correction curve of output voltages of a pH sensing electrode under different pH buffer solutions with pH values of about 2 to 12.

FIG. 4 is a plot showing a linear-correction curve of output voltages of a pH sensing electrode under different pH buffer solutions with pH values of about 2 to 12, according to a detecting scheme of FIG. 3. By the detecting scheme, a stabilization range of the sensibility of a device is determined by calculating a linearity correction curve of the reaction voltage.

Figure 5:
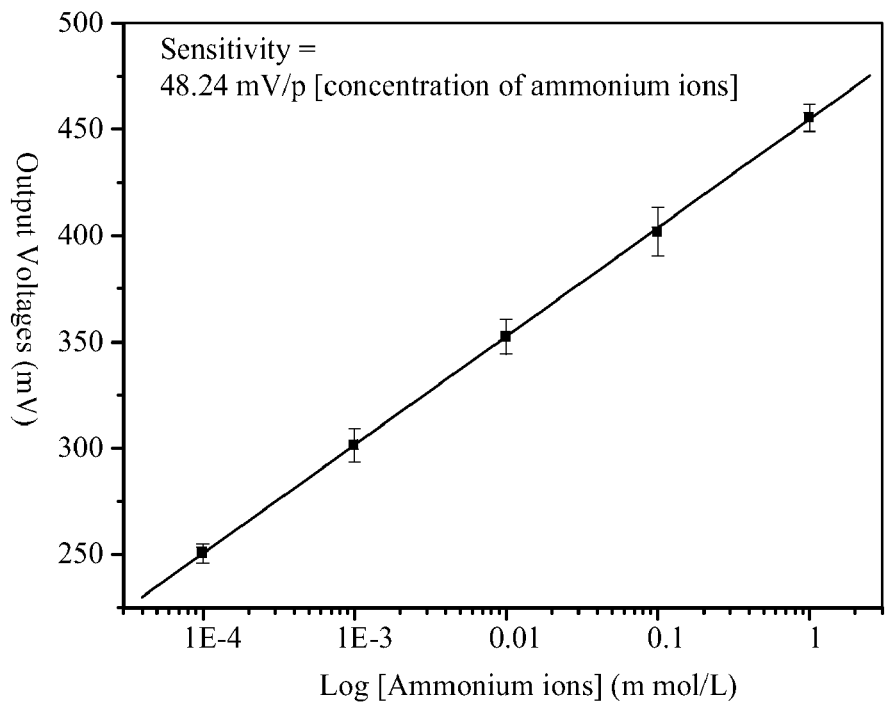
FIG. 5 is a plot showing a linear-correction curve of output voltages of an ammonium ion-selecting electrode under different ammonium ion solutions in a concentration range between 0.1 $\mu M$ to 1 $\mu M$.

FIG. 5 is a plot showing a linear-correction curve of output voltages of an ammonium ion-selecting electrode under different ammonium ion solutions in a concentration range between $10^{-4}$ μM to 1 μM, according to a detecting scheme of FIG. 3. By the detecting scheme, a stabilization range of the sensibility of a device is determined by calculating a linearity correction curve of the reaction voltage.

FIG. 6 is a plot showing curves of output voltages of a creatinine biosensor, according to a detecting scheme of FIG. 3. The biosensor is fabricated according to the process of FIG. 1. A sensing device of the biosensor is introduced into a buffer solution. The buffer solution has a pH value of about 7.5 and is without creatinine. After the voltage is stable, the sensing device is introduced into a creatinine solution, which solution has a concentration of about 6.7 μM and has a pH value of about 7.5. When the reaction time of the sensing device is smaller than 25 seconds, the output voltages of different creatinine sensors can be 90 percent of the maximum reaction voltage. The numbers of FIG. 6: an output voltage 15 of a creatinine biosensor made of a pH sensing electrode. The output voltage 15 are obtained when a sensing device of the biosensor is introduced into a creatinine solution. The creatinine solution has a concentration of about 6.7 μM and has a pH value of about 7.5.

A reaction voltages 16 is output from a creatinine biosensor made of an ammonium ion-selecting electrode. The reaction voltage 16 are obtained when a sensing device of the biosensor is introduced into an enzyme solution. The enzyme solution has a concentration of about 6.7 μM and has a pH value of about 7.5.

Figure 7:
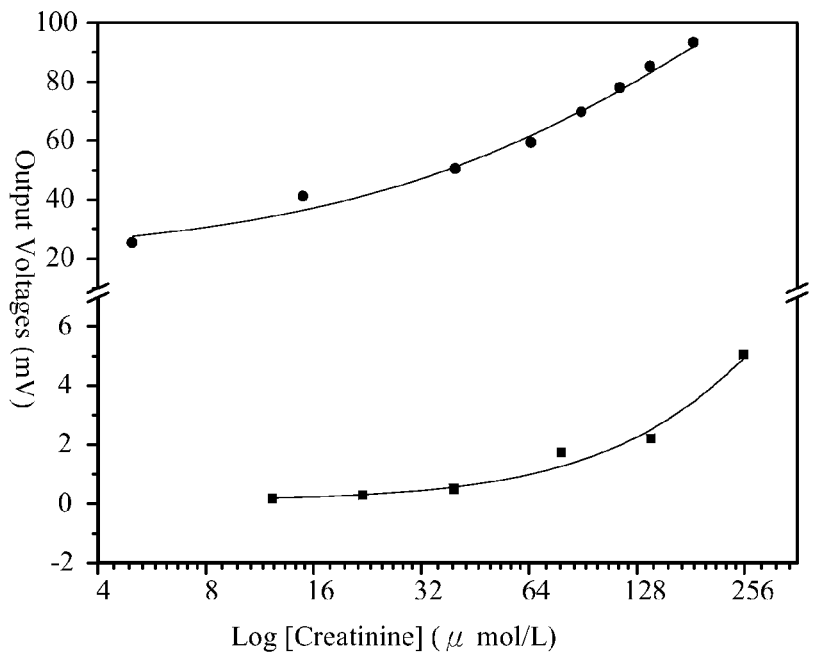
FIG. 7 is a plot showing a linear-correction curve of output voltages of an ammonium ion-selecting electrode under different creatinine solutions in a concentration range between 5 $\mu M$ to 255 $\mu M$.

FIG. 7 is a plot showing a linear-correction curve of output voltages of an ammonium ion-selecting electrode under different creatinine solutions in a concentration range between 5 μM to 255 μM, according to a detecting scheme of FIG. 3. The biosensor is fabricated according to the process of FIG. 1. Referring to FIG. 7, the detecting range of the sensing device is about 15 μM to about 185 μM. The low detecting limit is about 3 μM. The detecting range covers the creatinine detecting range of the human body standard (35 μM to 140 μM). The numbers of FIG. 7: a curve 17 of a set of output voltages, according to a creatinine biosensor made of a pH sensing electrode; a curve 18 of a set of output voltages, according to a creatinine biosensor made of an ammonium ion-selecting electrode.

Figure 8:
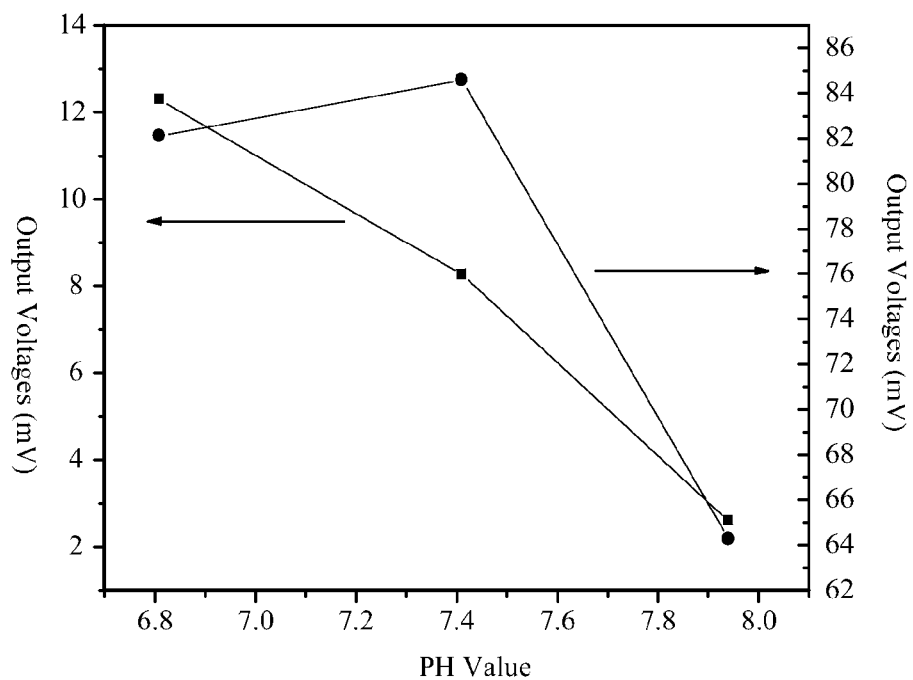
FIG. 8 is a plot showing maximum output voltages of a dual type potentiometric biosensor for creatinine detection, under different measured environments with different pH values.

FIG. 8 is a plot showing maximum output voltages of a biosensor for creatinine detection, under a concentration range of about 5 μM to about 255 μM, with different pH values, according to a detecting scheme of FIG. 3. The biosensor is fabricated according to the process of FIG. 1. As shown in FIG. 8, when the detecting environment has a PH value of about 6.5, a maximum output voltage is detected. The output voltage is detected by a creatinine biosensor made of a pH sensing electrode. When the detecting environment has a PH value of about 7.5, a maximum output voltage is detected. The output voltage is detected by a creatinine biosensor made of an ammonium ion-selecting electrode.

The numbers of FIG. 8: a maximum output voltage 19 of a creatinine biosensor made of a pH sensing electrode, for different detecting environments with different pH values; a maximum output voltage 20 of a creatinine biosensor made of an ammonium ion-selecting electrode, for different detecting environments with different pH values.

The above description of the preferred embodiments is expected to clearly expound the characteristics of the present invention but not expected to restrict the scope of the present invention. Those skilled in the art will readily observe that numerous modifications and alterations of the apparatus may be made while retaining the teaching of the invention. Accordingly, the above disclosure should be construed as limited only by the bounds of the claims.

What is claimed is:

1. A method for fabricating a biosensor, comprising:
depositing a sensing membrane on a substrate, wherein the sensing membrane is for detecting a pH value of a solution;
forming a conductive line on the substrate;
packaging the conductive line with the sensing membrane, wherein the conductive line serves as an external electrical contact point;
partially packaging the substrate, the sensing membrane and the conductive line with a package material, to leave a first sensing region and a second sensing region;
forming a sensing membrane for detecting a plurality of ammonium ions, on the second sensing region, wherein the formed sensing membrane serves as an ion-selecting and sensing region for detecting the ammonium ions;
forming a first creatinine enzyme membrane, on the sensing membrane and the second sensing region, by a photo-polymerisation reaction; and
connecting a readout circuit to the conductive line.

2. A biosensor, comprising:
a first sensing membrane, for detecting a pH value of a solution, the sensing membrane having a region serving as a first sensing region;
a second sensing membrane for detecting a plurality of ammonium ions, formed on the first sensing region of the first sensing membrane, wherein the second sensing membrane serves as an ion-selecting and sensing region for detecting the ammonium ions; and
a creatinine enzyme membrane, on the ion-selecting and sensing region, and on the first sensing region of the first sensing membrane.

* * * * *